United States Patent [19]

Kennedy

[11] Patent Number: 4,743,198
[45] Date of Patent: May 10, 1988

[54] PERIODONTAL SCALER

[76] Inventor: Joycelyn I. Kennedy, 1615 Perkins Road, Baton Rouge, La. 70808

[21] Appl. No.: 891,570

[22] Filed: Aug. 1, 1986

[51] Int. Cl.$^4$ .............................................. A61C 17/00
[52] U.S. Cl. .................................................. 433/143
[58] Field of Search ........................... 433/143, 144, 51

[56] References Cited

U.S. PATENT DOCUMENTS 1,397,395 11/1921 Bixler ................................... 433/143
4,643,676 2/1987 Jansheski ............................. 433/143

OTHER PUBLICATIONS

Suter Catalogue, p. 14, "Scalers" Suter Deutzl Mfg. Co., Jan. 1, 1981.
American Dental Manufacturing Company Catalog, 1982, pp. 28-31 and 54-58.
Misdom-Frank Instrument Company Catalog, 1984, pp. 6 and 11-15.
Karl Schumacher Dental Instrument Company, Inc., Catalog, Mar. 1980, pp. 87-96.
Silverman's Catalog, 1984, pp. 25-31.

Primary Examiner—Robert Peshock
Attorney, Agent, or Firm—James M. Pelton

[57] ABSTRACT

A periodontal scaler or currette having a shaft offset from the handle at an angle of 28° to 32° and a shank, which is offset back toward the central axis of the handle at an angle of 32° to 34° and a length equal to or 2.5 times greater than the shaft, ending in a curved blade in a plane orthogonal to the plane of the handle, shaft and shank.

11 Claims, 1 Drawing Sheet

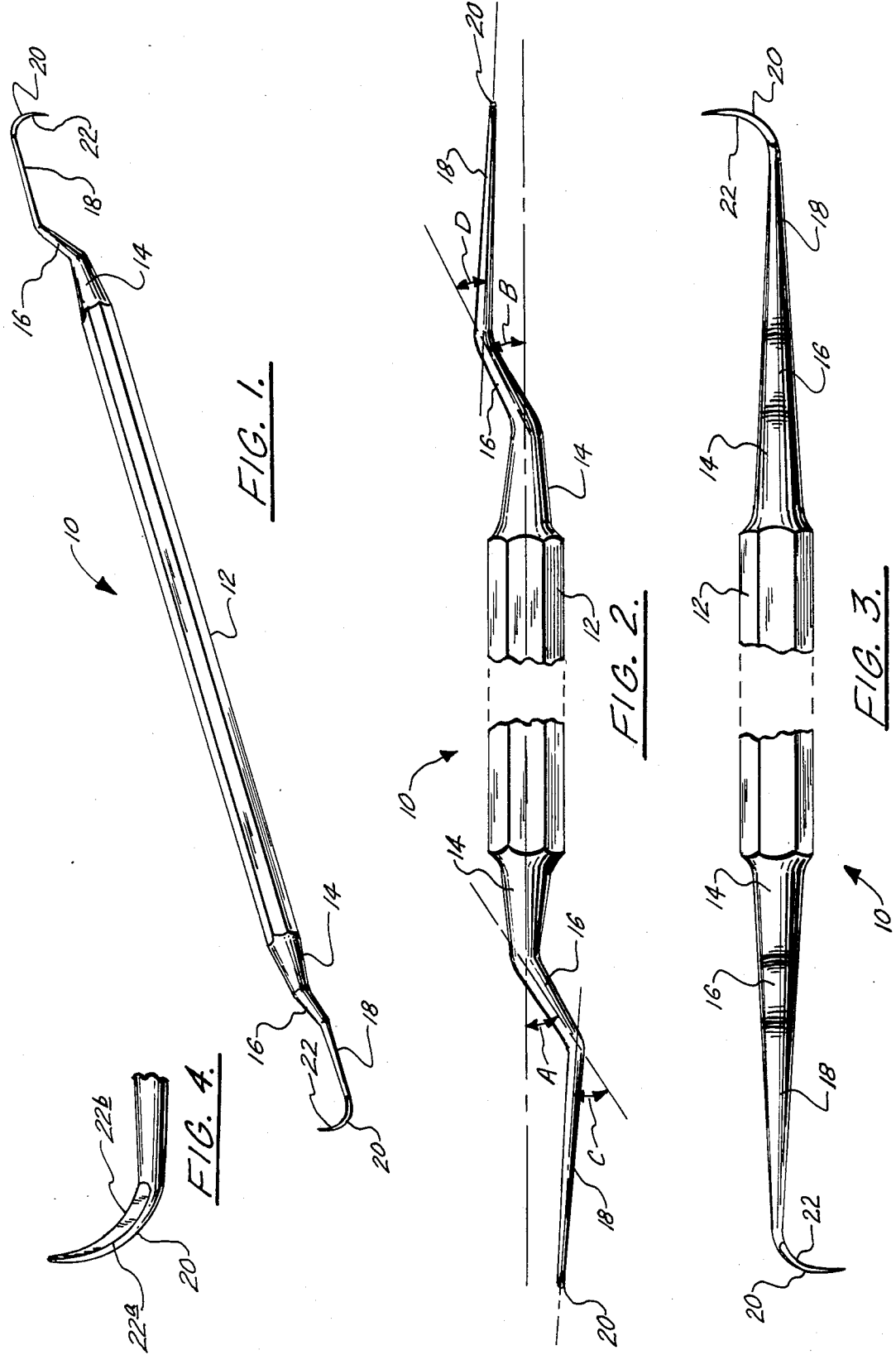

4,743,198

PERIODONTAL SCALER

BACKGROUND OF THE INVENTION

The present invention relates to novel dental instruments. Particularly, the present invention relates to useful and novel periodontal instruments such as periodontal scalers and curettes.

With the use of preventive dentistry and fluoride treatment, as well as good dental hygiene, human teeth are lasting longer and a major concern is now periodontal disease. Periodontics is a branch of dentistry that deals with diseases of the supporting and investing structures of the teeth including gums, cementum, periodontal membranes and alveolar bone. As a part of normal periodontal work, it is necessary to invade the pocket between the tooth structure and the gum in order to curettage diseased tissue and to scrape calculus and plaque found on the tooth structure below the gum line. A number of instruments are known for such work, including Gracey curettes, Barnhart curettes and Universal curettes and scalers; however, they suffer from a number of problems. Many of the instruments of the prior art require wide separation of the gum from the tooth structure in order to accomplish proper curettage and scaling. This results in subsequent inflammation and swelling. A great deal of pain is also associated with periodontal work using prior art instruments and the usual practice is for anesthesia to be administered when in performing periodontal work. In addition, the prior art instruments have not been of sufficient lengths to permit deep work and are wide in the blade portions such that too much tissue is excised. The known instruments have blade thicknesses of about 1 to 2 millimeters. Because periodontal work requires precision, a minor change in angle or size of an instrument results in major differences in the efficiency and effectiveness of the work. Thus, it is apparent that there is a need for periodontal curettes or scalers which are comfortable in handling and use, which are narrow enough and long enough to invade the periodontal pocket and still wide enough to be effective in curettage, which do not require anesthesia and which do not have an angle severe enough to widely separate the gum from the tooth root causing inflammation and swelling. The present invention provides such a periodontal scaler.

SUMMARY OF THE INVENTION

The present invention provides a periodontal scaler comprising:

(a) an elongated handle, (b) an offset shaft portion of regular tapering crosssection attached to one end of said handle which is offset from the central longitudinal axis of said handle at an angle of about 28° to about 32° and which has a length of about 6 to 10 millimeters, (c) a shank portion located at the opposite end of said shaft portion from said handle and offset from the central longitudinal axis of said shaft portion back toward the central longitudinal axis of said handle and located generally in the plane of both said handle and said shaft portion with an offset from the central longitudinal axis of said shaft portion of from about 32° to about 34°, said shank portion having a regular, tapering cross-section, which tapers at a rate less than said shaft portion and being of a length which is at least as long as said shaft portion, but not more than about 2.5 times as long as said shaft portion and not of sufficient length to meet the central longitudinal axis of said handle, and (d) a curved blade portion attached to the end of said shank portion opposite from said shaft portion located in a plane orthogonal to the plane of said handle, shank portion and shaft portion in which the curve of said curved blade portion circumscribes at least a quarter of a circular path, having a cutting edge on the inside portion of said curved blade portion and ending in a tapered, rounded point.

DESCRIPTION OF THE DRAWINGS

In the following figures of the drawing, like numbers represent like parts and;

FIG. 1 is a perspective view of a double-ended periodontal scaler of the present invention.

FIG. 2 is a broken top view of a periodontal scaler of the present invention showing the offset angles.

FIG. 3 is a broken elevational view of a periodontal scaler of the present invention showing the reverse curve blade in the double-ended version of the present invention and, FIG. 4 is a detailed perspective view of the blade portion of the periodontal scaler of the present invention.

DETAILED DESCRIPTION OF PREFERRED EMBODIMENTS OF THE INVENTION

As shown in FIGS. 1, 2 & 3, the periodontal scaler of this invention, generally indicated at 10, has a handle 12, which is generally elongated and can be of regular cross-section throughout, usually hexagonal, octagonal or circular. Preferably, the handle has grip aiding devices such as serrations or knurling. The handle is attached to the shaft portion 16, usually through a tapering transition piece 14, which forms part of the handle 12. The shaft portion 16 is also of regular, tapering cross-section and attached to one end of the handle 12 and is offset at an angle of about 28° to about 32° from the central longitudinal axis of the handle 12. As shown in broken FIG. 2 this angle is represented by angles A or B which are preferably equal and most preferably of reverse offset; that is, in the plane of the handle angle A would be offset to the left and angle B offset to the right from the central longitudinal axis when looking from right to left in FIG. 2. The shaft portion 16 is offset to provide direct access to the side of the tooth structure for easy invasion or insertion of the instrument into the pocket between the tooth structure and the gum, known in the industry as the periodontal pocket. Because of the offset of the shaft portion 16 from the central longitudinal axis of the handle 12, the hygenist or dentist can work directly in line with the tooth and the offset shaft portion 16 allows the instrument to line up with the outside or inside, as the case may be, of the tooth structure while the handle is directly over the tooth. This direct operation is a decidedly advantageous feature of the present invention. Prior art curettes or scalers generally have the operative end portion or blade directly in line with the central longitudinal axis of the handle even though there may be an offset to the shank of the instrument itself. The length of the shaft portion 16 can be usually about 6 to 10 millimeters and preferably is about 7.5 millimeters.

The end of the shaft portion 16 is connected to the shank portion 18 of the periodontal scaler 10 of the present invention. Shank portion 18 also has a regular, tapering cross-section which tapers at a rate less than that of the shaft portion. It has a length which is at least equal to and not more than about 2.5 times that of the shaft portion 16. The shank portion 18 is offset from the central longitudinal axis of the shaft portion 16 by an amount shown in angles C and D of FIG. 2. Preferably, angles C and D are equal and range from about 32° to about 34° from the central longitudinal axis of the shaft portion 16 back toward the central longitudinal axis of the handle 12.

Shank portion 18 ends in curved blade 20 which curves into a plane orthogonal to the plane of the handle 12, shaft portion 16, and shank portion 18, as shown more clearly in FIG. 3. The blade portion 20 curves through at least a quarter of a circular outline and ends in a tapered point. While the outside of the curved blade 20 portion is smooth and rounded, the machined edges and sides form, on the inside edges, two cutting edges 22, which are used to curettage diseased tissue and plaque from the surrounding tooth structure.

Because the shank portion 18 does not extend back to the central longitudinal axis of the handle 12 and because it is sufficiently long, but offset back towards that axis, it easily fits into the periodontal pocket without widely separating the tissue from the tooth. This is a further advantageous feature of the present invention, because the necessity of prior art periodontal curettes and scalers, requiring wide separation in order to operate efficiently, causes a great deal of pain and usually requires anesthesia in order to conduct the periodontal curettage and scaling. The present invention is accordingly easier to insert into the periodontal pocket and does not require wide separation of the tissue from the tooth structure. A further result of this large degree of separation is the tearing of fibers from the tooth structure and the damage of the tissue which causes inflammation and swelling. Such a condition usually requires two or three days to subside.

The curved blade portion 20 is more clearly illustrated with reference to FIG. 4 in which the outside curved portion 20 is shown and the cutting edges 22a and 22b produced by machining and stone finishing are shown in greater detail. The tapered, rounded point 24 does not gouge the tissue as would a sharply pointed instrument.

Although shown as a double-ended instrument, the instrument can be single-ended as well. However, this would require two instruments in order to obtain a left hand and right hand offset of the shaft portion in order to work on all portions of the periodontal structure. Periodontal scalers are usually made of carbon steel or stainless steel and those materials are useful for the present invention as well. However, recently, the use of titanium implants to anchor crown structures to the alveolar bone have limited the use of periodontal instrument materials since stainless steel marks and scratches the titanium implants. Thus, for use in periodontal work around titanium implant posts, a periodontal scaler or curette of the present invention would be better made from titanium. Where a titanium implant is not present, stainless steel is a preferred material for the periodontal scaler of the present invention. Thus, preferred materials for scalers of the present invention are stainless steel and titanium. Although the angles A, B, C & D can be varied somewhat in order to obtain the advantage of comfort and direct action, large variations are not possible. Further, the length of the shank portion is an advantage in deep scaling, however, it should not be so short that the offset shaft portion 16 contacts the top of the tooth structure or so long as to be flexible in working in the periodontal pocket.

Having described the periodontal scaler of the present invention, one skilled in the art would be aware of modification and variations within the spirit of the present invention. Therefore, it is desired that the present invention be limited only by the lawful scope of the following claims.

I claim:

1. A periodontal scaler comprising:
   (a) an elongated handle,
   (b) an offset shaft portion of regular tapering crosssection attached to one end of said handle which is offset from the central longitudinal axis of said handle at an angle of about 28° to about 32° and which has a length of about 6 to 10 millimeters,
   (c) a shank portion located at the opposite end of said shaft portion from said handle and offset from the central longitudinal axis of said shaft portion back toward the central longitudinal axis of said handle and located generally in the plane of both said handle and said shaft portion with an offset from the central axis of said shaft portion of from about 32° to about 34°, said shank portion having a regular, tapering cross-section, which tapers at a rate less than said shaft portion and being of a length which is at least as long as said shaft portion, but not more than 2.5 times as long as said shaft portion and not of sufficient length to meet the central longitudinal axis of said handle, and
   (d) a curved blade portion attached to the end of said shank portion opposite from said shaft portion located in a plane orthogonal to the plane of said handle, shank portion and shaft portion in which the curve of said curved blade portion circumscribes at least a quarter of a circular path, having a cutting edge on the inside portion of said curved blade portion and ending in a tapered, rounded point.

2. The scaler of claim 1 in which said handle has a generally regular polygonal or circular cross-sectioned portion and tapers through a transition portion at said offset shaft.

3. The scaler of claim 2 in which said handle, including said transition portion, said shaft portion, said shank portion and said curved blade portion are of one-piece construction.

4. The scaler of claim 1 in which said scaler is double-ended scaler.

5. The scaler of claim 4 in which the two ends of said scaler have reverse offsets in said shaft portion, so that the offset angle of the one end is opposite that of the other end.

6. The scaler of claim 5 in which the curved blade portions have reversed curves so that they extend in opposite directions.

7. The scaler of claim 1 in which the offset angle of the central longitudinal axis of said offset shaft portion is about 30° from the central longitudinal axis of said handle.

8. The scaler of claim 1 in which the central longitudinal axis of said shank portion is offset at an angle of about 33° from the central longitudinal axis of said offset shaft portion.

9. The scaler of claim 4 in which the offset angle of the central longitudinal axis of said offset shaft portion is about 30° from the central longitudinal axis of said handle.

10. The scaler of claim 9 in which the central longitudinal axis of said shank portion is offset at an angle of about 33° from the central longitudinal axis of said offset shaft portion.

11. The scaler of claim 1 being composed of stainless steel or titanium metal.

* * * * *